United States Patent
Just et al.

(10) Patent No.: US 7,598,409 B2
(45) Date of Patent: Oct. 6, 2009

(54) SPECIFIC PROCESS FOR PREPARING SILICON COMPOUNDS BEARING FLUOROALKYL GROUPS BY HYDROSILYLATION

(75) Inventors: Eckhard Just, Rheinfelden (DE); Sabine Giessler, Rheinfelden (DE); Peter Jenkner, Rheinfelden (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/583,553

(22) PCT Filed: Oct. 21, 2004

(86) PCT No.: PCT/EP2004/052608

§ 371 (c)(1),
(2), (4) Date: Jun. 19, 2006

(87) PCT Pub. No.: WO2005/058919

PCT Pub. Date: Jun. 30, 2005

(65) Prior Publication Data

US 2007/0112213 A1 May 17, 2007

(30) Foreign Application Priority Data

Dec. 19, 2003 (DE) ................ 103 61 893

(51) Int. Cl.
*C07F 7/04* (2006.01)

(52) U.S. Cl. .............. 556/466; 556/465; 556/479; 556/485

(58) Field of Classification Search ........... 556/466, 556/479, 465, 485
See application file for complete search history.

(56) References Cited

U.S. PATENT DOCUMENTS

| 4,089,882 | A | | 5/1978 | Takamizawa et al. |
|---|---|---|---|---|
| 5,262,557 | A | * | 11/1993 | Kishita et al. ............... 556/448 |
| 5,420,323 | A | * | 5/1995 | Jung et al. .................. 556/415 |
| 5,646,325 | A | | 7/1997 | Monkiewicz et al. |
| 5,869,728 | A | * | 2/1999 | Jenker et al. ................ 556/479 |
| 6,113,815 | A | * | 9/2000 | Elfersy et al. ............... 252/588 |
| 6,114,562 | A | * | 9/2000 | Fukuda et al. .............. 556/485 |
| 6,177,582 | B1 | | 1/2001 | Jenker et al. |
| 6,177,585 | B1 | * | 1/2001 | Chen et al. .................. 556/479 |
| 6,251,989 | B1 | | 6/2001 | Edelmann et al. |
| 6,255,516 | B1 | | 7/2001 | Jenker et al. |
| 6,361,871 | B1 | | 3/2002 | Jenker et al. |
| 6,426,150 | B1 | | 7/2002 | Jenker et al. |
| 6,713,186 | B1 | | 3/2004 | Jenker et al. |
| 6,858,746 | B2 | | 2/2005 | Giessier et al. |
| 2005/0245628 | A1 | | 11/2005 | Hubel et al. |
| 2009/0054683 | A1 | | 2/2009 | Bueker et al. |

OTHER PUBLICATIONS

U.S. Appl. No. 10/567,023, filed Feb. 3, 2006, Giessler, et al.
U.S. Appl. No. 10/552,918, filed Oct. 11, 2005, Albert, et al.
U.S. Appl. No. 10/556,040, filed Nov. 8, 2005, Albert, et al.
U.S. Appl. No. 10/583,553, filed Jun. 19, 2006, Just, et al.
U.S. Appl. No. 12/376,576, filed Feb. 6, 2009, Lang, et al.
U.S. Appl. No. 12/375,033, filed Jan. 26, 2009, Lang, et al.
U.S. Appl. No. 12/376,633, filed Feb. 6, 2009, Lang, et al.
U.S. Appl. No. 12/376,786, Feb. 9, 2009, Lang, et al.

* cited by examiner

*Primary Examiner*—Sikarl A Witherspoon
*Assistant Examiner*—Chukwuma O Nwaonicha
(74) *Attorney, Agent, or Firm*—Oblon, Spivak, McClelland, Maier & Neustadt, L.L.P.

(57) ABSTRACT

The present invention relates to a process for preparing silicon compounds bearing fluoroalkyl groups by hydrosilylation of a fluoroolefin in the presence of a hydrosilylation catalyst, which comprises initially charging and heating a hydrogenchlorosilane, then metering in the fluoroolefin and reacting the reaction mixture and subsequently isolating the hydrosilylation product.

14 Claims, No Drawings

SPECIFIC PROCESS FOR PREPARING SILICON COMPOUNDS BEARING FLUOROALKYL GROUPS BY HYDROSILYLATION

The present invention relates to a specific process for preparing silicon compounds bearing fluoroalkyl groups by hydrosilylation of a fluoroolefin in the presence of a Pt-containing hydrosilylation catalyst. Furthermore, the hydrosilylation product can be esterified to form a corresponding alkoxysilane.

The hydrosilylation of olefins in the presence of a catalyst and esterification processes have been known for a long time and are important processes for preparing organofunctional silanes.

DE 28 51 456 A1 discloses a continuous hydrosilylation process which is carried out at a pressure of up to 6 bar abs. in the presence of a hydrosilylation catalyst used in the homogeneous phase in a tube reactor through which a liquid phase of the components flows. The preparation of the catalyst used in this mode of operation is also quite complicated.

EP 0 075 864 A2 and EP 0 075 865 A2 relate to the preparation of hexafluoropropyloxyalkylsilanes and tetrafluoroethyloxyalkylsilanes by hydrosilylation in the presence of a hydrosilylation catalyst, with fluoro-functional olefin ethers being used as olefin component. These processes, too, are carried out continuously at a pressure of up to 6 bar abs. in a tube reactor through which liquid phase flows.

Since according to EP 0 652 222 A1, a Pt catalyst or Pt(0) complex, which may, if appropriate, be used as a solution in an inert solvent, is not active enough alone, a peroxide has to be used to activate the catalyst in order to improve the economics.

Furthermore, EP 0 838 467 A1 teaches that the olefin component and the Pt(0) complex are initially charged as a solution in xylene or toluene and the hydrogenchlorosilane is metered in at room temperature, with the temperature rising suddenly to about 120° C. and above. The olefin and hydrogenchlorosilane components are used in a molar ratio of =1:1 in this process. The process can also be carried out under superatmospheric pressure. Yields of up to 99% by weight and purities of >97 GC-TCD-% by area are achieved in this process. However, a disadvantage is that a low activity of the catalyst is also observed here. However, as our own studies show, these processes are very sensitive to impurities. If a reaction in one of the processes mentioned does not start, the entire batch is usually unusable and has to be discarded, including the high-priced fluoroolefin component.

It is therefore an object of the present invention to provide a further process for preparing fluoroalkylchlorosilanes and also, in the further course of the process, corresponding fluoroalkylalkoxysilanes. A particular objective is to alleviate the abovementioned disadvantages.

This object is achieved, according to the invention, by the features of the claims.

It has surprisingly been found that fluoroalkylchlorosilanes can also be prepared on an industrial scale in a simple economical and reliable manner by hydrosilylation of fluoroolefins in the presence of a Pt catalyst which may, if appropriate, be used as a solution in an essentially inert solvent, even without additional catalyst activation, when a hydrogenchlorosilane is firstly placed in a stirred tank reactor, the contents are heated, preferably preheated to from about 90 to 120° C. under superatmospheric pressure, and the fluoroolefin is only then metered in and the hydrosilylation product is subsequently isolated from the product mixture, for example by distillation.

The fluoroolefin is appropriately metered in with good mixing and over a period of at least 2 hours, preferably from 4 to 15 hours, in particular from 6 to 8 hours, with a pressure of from 1 to 50 bar abs., preferably from 2 to 20 bar abs., in particular from 3 to 10 bar abs., being set and the metering time of the fluoroolefin being based on 1 t of trichlorosilane.

The reaction generally proceeds exothermically and in the present process is advantageously carried out at a temperature in the range from 85 to 120° C., preferably from 90 to 115° C., in particular from 100 to 110° C.

The hydrosilylation is generally also carried out under a blanket of protective gas, for example under nitrogen.

The product yield of the present process is significantly above that of comparable processes. The fluoroalkylsilane obtained in this way has a purity of >99 GC-TCD-% by area.

The fluoroalkylchlorosilane obtained according to the invention can then be esterified with an alcohol in a manner known per se. The use of methanol results, as is known, in elimination of hydrogen chloride to form the corresponding fluoroalkylmethoxysilanes, the use of ethanol gives the corresponding ethoxysilanes, the use of propanol gives the corresponding propoxysilanes, etc.

Furthermore, the unreacted trichlorosilane and solvent obtained in the distillation can be reused as starting components.

The process of the invention is particularly notable for the reduced sensitivity of the reaction to impurities in the olefin, since if the reaction does not start, the process can be stopped in good time in the present process, as a result of which the extremely expensive fluoroolefin is saved and does not have to be discarded as an unusable mixture.

In addition, the present process can be operated at a higher temperature, which results in even better utilization of the catalyst activity.

The present invention accordingly provides a process for preparing a silicon compound bearing at least one fluoroalkyl group by hydrosilylation of a fluoroolefin in the presence of a Pt-containing catalyst, which comprises initially charging and heating a hydrogenchlorosilane, then metering in the fluoroolefin and reacting the reaction mixture and subsequently isolating the hydrosilylation product.

In particular, the following procedure can be employed according to the invention:

(i) a hydrogenchlorosilane is initially charged, heated, the hydrosilylation catalyst dissolved in an inert solvent is added and the fluoroolefin is then metered in or (ii) a hydrogenchlorosilane is initially charged, heated and a mixture of fluoroolefin, hydrosilylation catalyst and optionally solvent is metered in or (iii) a mixture of hydrogenchlorosilane and the hydrosilylation catalyst dissolved in a solvent are initially charged, heated and the fluoroolefin is metered in.

It has also been found that the purity of the fluoroolefins used also has a significant influence on the platinum-catalyst hydrosilylation process. Preference is given to using a fluoroolefin of defined purity in the present process.

Thus, it has been found that fluoroalkylchlorosilanes can advantageously be prepared in a simple, economical and reliable manner by hydrosilylation of fluoroolefins in the presence of a Pt catalyst, even on an industrial scale and without unexpected catalyst deactivation, when a fluoroolefin having a very low iodide or iodine (hereinafter referred to as iodine for short) content is used.

The present process according to the invention is preferably carried out using a fluoroolefin containing less than 150 ppm by weight of iodine, particularly preferably less than 100 ppm by weight of iodine, very particularly preferably less than 50 ppm by weight of iodine, in particular less than 10 ppm by weight of iodine, i.e. down to the detection limit for iodide or iodine.

The process of the invention is likewise preferably carried out using fluoroolefins having a content of dienes which, as is known per se, can be formed by dimerization of the corresponding monomeric olefins of less than 100 ppm by weight, particularly preferably <50 ppm by weight, very particularly preferably <20 ppm by weight, in particular fluoroolefins containing from 1 to 10 ppm by weight or less of dienes.

The fluoroolefin used in the present process should also have a water content of less than 100 ppm by weight, preferably =50 ppm by weight.

In general, the process of the invention can be carried out by placing the hydrogen-chlorosilane in a stirred vessel which may be heatable or coolable, is appropriately provided with a stirring device and/or reflux cooling and can be operated under inert gas, for example nitrogen, and under superatmospheric pressure, and heating it and metering in the fluoroolefin in the presence of a Pt-containing hydrosilylation catalyst and, if appropriate, a solvent. The reaction mixture is advantageously then allowed to react further and the product mixture obtained in this way can be worked up. A fluoroalkylchlorosilane obtained in this way can subsequently be esterified with an alcohol in a manner known per se to give the corresponding fluoroalkylalkoxysilane.

Thus, the process of the invention is preferably carried out batchwise in a stirred tank reactor. The present process can also be carried out continuously.

In the process of the invention, hydrogenchlorosilane and fluoroolefin are preferably used in a molar ratio of from 3:1 to 0.5:1, particularly preferably from 2:1 to 0.8:1, in particular from 1:1 to 1.1:1.

As Pt-containing hydrosilylation catalyst, it is possible to use, for example, platinum-olefin complexes, platinum-alcohol or platinum-alkoxide complexes, reaction products of $H_2PtCl_6 \cdot 6H_2O$ and acetone or cyclohexanone and also platinum-vinylsiloxane complexes, in particular hexachloroplatinic acid or platinum(0) complexes, in the process of the invention. The platinum catalyst is appropriately used in a homogeneous phase. Particular preference is given to using Pt(0)-divinyltetramethyldisiloxane (hereinafter also referred to as Karstedt catalyst), with the catalyst advantageously being used as a solution in an inert solvent. Preferred inert solvents are, for example, toluene and xylene. The process of the invention is advantageously carried out using a catalyst solution having a platinum content of from 0.01 to 20% by weight.

In the process of the invention, Pt catalyst and silane component are preferably used in a molar ratio of Pt to hydrogenchlorosilane of from 1:100000 to 1:1000, particularly preferably from 1:50 000 to 1:5000, in particular from 1:30 000 to 1:10 000.

In particular, the process of the invention is carried out using at least one hydrogenchlorosilane from the series $H_{(4-a-b)}SiR_aX_b$ (I), where the groups R are identical or different and R is a linear, branches or cyclic alkyl group having from 1 to 20 carbon atoms or an aryl group, X is Cl or Br and a=0, 1, 2 or 3 and b=0, 1, 2 or 3 and 1=(a+b)=3, for example trichlorosilane, methyldichlorosilane, dimethylchlorosilane.

Preference is also given to using at least one fluoroolefin of the formula II

where $R^1$ is a monofluorinated, oligofluorinated or perfluorinated alkyl group having from 1 to 12 carbon atoms or a perfluorinated aryl group, Y is a —$CH_2$—, —O—, —O—$CH_2$—, —S— group and m is 0 or 1. Examples of such fluoroolefins are: $CF_3(CF_2)_nCH=CH_2$ where n=3, 5, 7, 9, 11 and $HCF_2CF_2OCH_2CH=CH_2$.

Particularly useful fluoroolefins are, for example, 3,3,3-trifluoro-1-propene, 3,3,4,4,5,5,6,6,7,7,8,8,8-tridecafluorooctene, 3,3,4,4,5,5,6,6,7,7,8,8,9,9,10,10,10-tridecafluorodecene, 1,1,2,2-tetrafluoroethyl allyl ether, 3,3,4,4,5,5,6,6,7,7,8,8,9,9,-10,10,10-heptadecafluorooctene, 3,3,4,4,5,5,6,6,7,7,8,8,9,9,10,10,11,11,12,12,12-hencosafluorooctene or 3,3,4,4,5,5,6,6,7,7,8,8,9,9,10,10,11,11,12,12,13,13,14,14,14-pentacosafluorooctene.

In the process of the invention, the hydrogenchlorosilane initially charged in the first step is preferably heated to a temperature in the range from 85 to 120° C., particularly preferably from 90 to 115° C., in particular from 100 to 110° C.

In the present process, an inert solvent, solvent mixture or diluent, for example xylene, toluene, can be additionally added to the reaction mixture.

Furthermore, the metered addition of the fluoroolefin in the second step of the process of the invention is preferably carried out at a pressure of from 1 to 15 bar abs., in particular from 2 to 9 bar abs.

In the process of the invention, the fluoroolefin is appropriately introduced at a rate of, based on an initial charge of 1 t of chlorosilane, from 50 to 300 l/h, preferably from 100 to 230 l/h, in particular from 140 to 180 l/h, i.e. the metered addition of the fluoroolefin and the reaction of the reaction components advantageously occurs over a period of from 5 to 12.5 hours, preferably from 6 to 10 hours, in particular about 8 hours.

The crude product or product mixture obtained in this way can then be worked up by distillation in the following step to isolate the hydrosilylation product which can subsequently be esterified with an alcohol in a manner known per se. The use of methanol results, as is known, in elimination of hydrogen chloride to form the corresponding fluoroalkylmethoxysilanes, the use of ethanol gives the corresponding ethoxysilanes, the use of propanol gives the corresponding propoxysilanes, etc.

The esterification is preferably carried out using a slight excess of alcohol, particularly preferably an excess of from 0.1 to 10% by weight, in particular from 1 to 5% by weight. The product is then generally neutralized with alkali metal alkoxide and the salt formed is separated off. The alcohol used in the esterification is usually denatured with a maximum of 1% of methyl ethyl ketone. However, alcohol denatured with petroleum ether or pure alcohol can also be used advantageously.

Examples of fluoroalkyl-functional silanes which can be obtained advantageously by the present process according to the invention are tridecafluoro-1,1,2,2-tetrahydro-octyltrichlorosilane, correspondingly tridecafluoro-1,1,2,2-tetrahydrooctyltrimethoxysilane and tridecafluoro-1,1,2,2-tetrahydrooctyltriethoxysilane, heptadecafluoro-1,1,2,2-tetrahydrodecyltrichlorosilane, heptadecafluoro-1,1,2,2-tetrahydrodecyltriethoxysilane, heptadecafluoro-1,1,2,2-tetrahydrodecyltrimethoxysilane, $C_{10}F_{21}$ $C_2H_4SiCl_3$, $C_{10}F_{21}C_2H_4Si(OCH_3)_3$, $C_{10}F_{21}C_2H_4Si(OC_2H_5)_3$, $C_{12}F_{25}C_2H_4SiCl_3$, $C_{12}F_{25}C_2H_4Si(OCH_3)_3$, $C_{12}F_{25}C_2H_4Si(OC_2H_5)_3$, to name only a few examples.

The present invention is illustrated by the following experiments:

COMPARATIVE EXAMPLE 1

120 g of 3,3,4,4,5,5,6,6,7,7,8,8,8-tridecafluorooctene (iodine content=170 ppm by weight) and 0.1733 g of CPC072 (Pt(0)-divinyltetramethyldisiloxane in xylene, containing 2% by weight of Pt), corresponding to a molar ratio of Pt to fluoroolefin of 1:20 000, are placed in a 250 ml stirred apparatus provided with a dropping funnel and, at ambient pressure, 52 g of trichlorosilane are metered in under nitrogen over the reaction time of 6 hours. The reaction temperature is from 86 to 93° C. The yield of trichloro(3,3,4,4,5,5,6,6,7,7,8,8,8-tridecafluorooctyl)silane after the end of the reaction, based on the 3,3,4,4,5,5,6,6,7,7,8,8,8-tridecafluorooctene used, is 2.6%.

COMPARATIVE EXAMPLE 2

120 g of 3,3,4,4,5,5,6,6,7,7,8,8,8-tridecafluorooctene (iodine content=6.5 ppm by weight) and 0.1733 g of CPC072 (Pt(0)-divinyltetramethyldisiloxane in xylene, containing 2% by weight of Pt), corresponding to a molar ratio of Pt to fluoroolefin of 1:20 000, are placed in a 250 ml stirred apparatus provided with a dropping funnel and, at ambient pressure, 52 g of trichlorosilane are metered in under nitrogen over the reaction time of 4.7 hours. The reaction temperature is from 86 to 93° C. The yield of trichloro(3,3,4,4,5,5,6,6,7,7,8,8,8-tridecafluorooctyl)silane after the end of the reaction, based on the 3,3,4,4,5,5,6,6,7,7,8,8,8-tridecafluorooctene used, is 87%.

EXAMPLE 1

100 g of trichlorosilane are placed in a 350 ml steel autoclave at room temperature, 0.35 g of CPC072 (Pt(0)-divinyltetramethyldisiloxane in xylene, containing 2% by weight of Pt) is added under a blanket of nitrogen and 221.4 g of 3,3,4,4,5,5,6,6,7,7,8,8,8-tridecafluorooctene (iodine content=170 ppm by weight), corresponding to a molar ratio of Pt to fluoroolefin of 1:20 000, are subsequently metered in at an internal reactor pressure of from 5.8 to 6 bar abs. over a period of 4.5 hours by means of a pump. The reaction temperature is set to from 116 to 126° C. at about 3 bar abs. The yield of trichloro-(3,3,4,4,5,5,6,6,7,7,8,8,8-tridecafluorooctyl)silane after the end of the reaction, based on the 3,3,4,4,5,5,6,6,7,7,8,8,8-tridecafluorooctene used, is 82%.

EXAMPLE 2

100 g of trichlorosilane are placed in a 350 ml steel autoclave at room temperature, heated and 0.35 g of CPC072 (Pt(0)-divinyltetramethyldisiloxane in xylene, containing 2% by weight of Pt) are added under a blanket of nitrogen and 242.2 g of 3,3,4,4,5,5,6,6,7,7,8,8,8-tridecafluorooctene (iodine content=8 ppm by weight), corresponding to a molar ratio of Pt to fluoroolefin of 1:20 000, are subsequently metered in at a reactor pressure of from 2 bar to 6 bar abs. over a period of 4 hours by means of a pump. The reaction temperature is from 102 to 116° C. After a time of 6.5 hours, a yield of trichloro(3,3,4,4,5,5,6,6,7,7,8,8,8-tridecafluorooctyl)silane, based on the 3,3,4,4,5,5,6,6,7,7,8,8,8-tridecafluorooctene used, of 94% is achieved. 320 g of trichloro-(3,3,4,4,5,5,6,6,7,7,8,8,8-tridecafluorooctyl)silane are firstly placed in a 1 l stirred apparatus provided with a dropping funnel and nitrogen blanketing. This initial charge is heated until the liquid in the apparatus has reached a temperature of about 100° C. 91.8 g of ethanol (denatured with 1% of methyl ethyl ketone) are then metered in over a period of about 4 hours. After the end of the metered addition, the mixture is stirred for about 2 hours more, then cooled before 55.0 g of (20% strength) sodium ethoxide are added. The yield, based on trichloro(3,3,4,4,5,5,6,6,7,7,8,8,8-tridecafluorooctyl)silane, is 91.6%.

EXAMPLE 3

95 g of trichlorosilane are placed in a 350 ml steel autoclave at room temperature, heated and 0.21 g of CPC072 (Pt(0)-divinyltetramethyldisiloxane in xylene, containing 2% by weight of Pt) are added under a blanket of nitrogen. This corresponds to a molar ratio of Pt to fluoroolefin of 1:33 000. 242 g of 3,3,4,4,5,5,6,6,7,7,8,8,8-tridecafluorooctene (iodine content=6.5 ppm by weight) together with an additional 0.21 g of CPC072 are subsequently metered in at a reactor pressure of from 5.7 bar to 7.5 bar abs. over a period of 3 hours by means of a pump (final ratio of Pt to fluoroolefin=1:17 000). The reaction temperature is from 106 to 124° C. After a time of 4.8 hours, a yield of trichloro(3,3,4,4,5,5,6,6,7,7,8,8,8-tridecafluorooctyl)silane, based on the 3,3,4,4,5,5,6,6,7,7,8,8-tridecafluorooctene used, of 93% is achieved.

The invention claimed is:

1. A process for preparing a silicon compound bearing at least one fluoroalkyl group by hydrosilylation of a fluoroolefin in the presence of a Pt-containing hydrosilylation catalyst, the process comprising:
   initially charging and heating a hydrogenchlorosilane;
   metering in the fluoroolefin and reacting the reaction mixture; and
   subsequently isolating the hydrosilylation product, and
   wherein the Pt-containing hydrosilylation catalyst consists of a hexachloroplatinic acid or a Pt(0) complex;
   wherein the fluoroolefin has an iodine content from 6.5 ppm to 170 ppm by weight, a diene content from 1 ppm to less than 100 ppm by weight, and a water content of less than 100 ppm by weight.

2. The process as claimed in claim 1, wherein,
   (i) the hydrogenchlorosilane is initially charged, heated, the hydrosilylation catalyst dissolved in an inert solvent is added and the fluoroolefin is then metered in; or
   (ii) the hydrogenchlorosilane is initially charged, heated and a mixture of fluoroolefin, hydrosilylation catalyst and optionally solvent is metered in; or
   (iii) a mixture of the hydrogenchlorosilane and the hydrosilylation catalyst dissolved in a solvent are initially charged, heated, and the fluoroolefin is metered in.

3. The process as claimed in claim 1, wherein the initially charged hydrogen-chlorosilane or the initially charged hydrogenchlorosilane-containing mixture is heated to a temperature in the range from 85 to 120° C.

4. The process as claimed in claim 1, wherein hydrogenchlorosilane and fluoroolefin are used in a molar ratio of from 3:1 to 0.5:1.

5. The process as claimed in claim 1, wherein toluene or xylene is used as an inert solvent.

6. The process as claimed in claim 1, wherein the catalyst is used in a molar ratio of Pt to hydrogenchlorosilane of from 1:100 000 to 1:100.

7. The process as claimed in claim 1, wherein at least one hydrogenchlorosilane of the formula (I)

$$H_{(4-a-b)}SiR_aX_b \qquad (I),$$

wherein the groups R are identical or different and R is a linear, branched or cyclic alkyl group having from 1 to 20 carbon atoms or an aryl group, the X is Cl,
a=0, 1, 2 or 3,
b=0, 1, 2 or 3, and
1≦(a+b)≦3.

8. The process as claimed in claim 1, wherein at least one fluoro-olefin of the formula II

 (II), wherein $R^1$ is a monofluorinated, oligofluorinated, or perfluorinated alkyl group having from 1 to 12 carbon atoms or a perfluorinated aryl group, Y is a —CH$_2$—, —O—, —O—CH$_2$—, or —S—group, and m is 0 or 1.

9. The process as claimed in claim 1, wherein the fluoroolefin is selected from the group consisting of 3,3,3-trifluoro-1-propene,
3,3,4,4,5,5,6,6,7,7,8,8,8-tridecafluorooctene,
3,3,4,4,5,5,6,6,7,7,8,8,9,9,10,10,10-tridecafluorooccene,
1,1,2,2-tetrafluoroethyl allyl ether,
3,3,4,4,5,5,6,6,7,7,8,8,9,9,10,10,10-heptadecafluorodecene,
3,3,4,4,5,5,6,6,7,7,8,8,9,9,10,10,11,11,12,12,12-hencosafluorooctene, and
3,3,4,4,5,5,6,6,7,7,8,8,9,9,10,10,11,11,12,12,13,13,14,14,14-pentacosafluorooctene.

10. The process as claimed in claim 1, wherein the fluoroolefin is added to the initially charged hydrogenchiorosilane as set forth in (i) or (ii) or (iii) at a pressure of from 1 to 15 bar abs.

11. The process as claimed in claim 1, wherein the fluoroolefin is metered in at a rate of from 50 to 300 l/h, based on 1 t of chlorosilane.

12. The process as claimed in claim 1, wherein the reaction is carried out at a temperature in the range from 85 to 120° C. and a pressure of from 1.5 to 50 bar abs. for a period of from 4 to 20 hours.

13. The process as claimed in claim 1, wherein the hydrosilylation product is isolated from the product mixture by distillation and is subsequently esterified with an alcohol, wherein the alcohol is used in an excess of from 0.1 to 10% and the alcohol used is denatured with ≦1% by weight of methyl ethyl ketone or petroleum ether.

14. The process as claimed in claim 1 performed batchwise in a stirred tank reactor.

* * * * *